United States Patent [19]

Garsky

[11] 3,991,041
[45] Nov. 9, 1976

[54] (PHE₃-ALA)₁-SOMATOSTATIN

[75] Inventor: Victor M. Garsky, Havertown, Pa.

[73] Assignee: American Home Products Corporation, New York, N.Y.

[22] Filed: Dec. 18, 1975

[21] Appl. No.: 642,107

[52] U.S. Cl. .......................... 260/112.5 R; 424/177
[51] Int. Cl.² ................. C07C 103/52; C07G 7/00; A61K 37/00
[58] Field of Search .............................. 260/112.5 S

[56] References Cited
UNITED STATES PATENTS 3,904,594  9/1975  Guillemin et al. ............ 260/112.5 S Primary Examiner—Lewis Gotts
Assistant Examiner—Reginald J. Suyat
Attorney, Agent, or Firm—Richard K. Jackson

[57] ABSTRACT

The growth hormone release inhibiting compound:

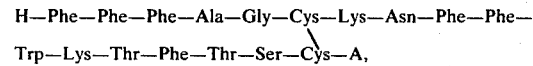

the corresponding linear heptadecapeptide, non-toxic acid addition salts and intermediates therefore are herein described, in which Trp is D-tryptophyl or L-tryptophyl and each of the other optically active amino acid moieties are of the L-configuration and A represents —OH, —NH₂, dimethylamino, alkylamino of 1–5 carbon atoms or phenethylamino.

11 Claims, No Drawings

(PHE$_3$-ALA)$_1$-SOMATOSTATIN

BACKGROUND OF THE INVENTION

The structure of the growth hormone release inhibiting factor, somatostatin, has been determined by Brazeau et al., Science, 179, 77(1973). Several techniques for synthesizing somatostatin have been reported in the literature, including the solid phase method of Rivier, J.A.C.S. 96, 2986(1974) and the solution methods of Sarantakis et al., Biochemical Biophysical Research Communications 54, 234(1973) and Immer et al., Helv. Chim. Acta, 57, 730(1974).

DESCRIPTION OF THE INVENTION

In accordance with this invention, there is provided a growth hormone release inhibiting compound of the formula:

L-Phe-L-Phe-L-Phe-L-Ala-Gly-L-Cys-L-Lys-L-Asn-L-Phe-L-Phe-X-Trp-L-Lys-L-Thr-L-Phe-L-Thr-L-Ser-L-Cys-A cyclic (6 → 17) disulfide, where X represents the D- or L-configuration of the tryptophyl moiety, and A represents —OH, —NH$_2$, dimethylamine, alkylamino of 1 to 5 carbon atoms or phenethylamino, the non-cyclic form of the heptadecapeptide, non-toxic acid addition salts thereof, and protected intermediates useful for the synthesis of the heptadecapeptide. The heptadecapeptides of this invention are useful in the treatment of conditions characterized by excessive growth hormone production, such as diabetes mellitus and acromegaly. The cyclic and linear forms of the heptadecapeptides of this invention decrease blood serum concentrations of growth hormone and glucagon without significantly reducing the concentration of insulin, a decided advantage in treatment of diabetes mellitus.

The heptadecapeptides of this invention are prepared by solid phase methodology. The solid phase method of preparing the heptadecapeptides of this invention is generally known in the art and is described by Merrifield, J.A.C.S., 85, 2149(1963). The resin support employed may be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced, fully protected amino acid.

The α-amino and sulfhydryl protected cysteine is coupled to the chloromethylated resin according to the procedure of Gisin, Helv. Chim. Acta., 56, 1476 (1973). Following the coupling of the α-amino and sulfhydryl protected cysteine to the resin support, the α-amino protecting group is removed by standard methods employing trifluoroacetic acid in methylene chloride, trifluoroacetic acid alone or HCl in dioxane. The deprotection is carried out at a temperature between about 0° C. and room temperature. After removal of the α-amino protecting group the remaining α-amino protected amino acids are coupled, seriatim, in the desired order to obtain the product. Alternatively, multiple amino acid groups may be coupled by the solution method prior to coupling with the resin supported amino acid sequence. The selection of an appropriate coupling reagent is within the skill of the art. A particularly suitable coupling reagent is N,N$^1$-diisopropyl carbodiimide. Another suitable coupling reagent is N,N$^1$-dicyclohexycarbodiimide.

Each protected amino acid or amino acid sequence is introduced into the solid phase reactor in about a fourfold excess and the coupling is carried out in a medium of dimethylformamide: methylene chloride (1:1) or in dimethylformamide or methylene chloride alone. In cases where incomplete coupling occurred the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

At the conclusion of the construction of the polypeptido resin, the fully protected intermediate represents the structural formula:

R$^1$-Phe-Phe-Phe-Ala-Gly-Cys(R$^2$) Lys(R$^3$)-Asn-Phe-Phe-X-Trp-Lys(R$^4$)-Thr(R$^5$)-Phe-Thr(R$^6$)-Ser(R$^7$) Cys(R$^8$)-O-CH$_2$-[polystyrene resin support], which is totally deprotected and removed from the Resin support by treatment with liquid hydrofluoric acid in the presence of anisole to yield the linear heptadecapeptide H-L-Phe-L-Phe-L-Phe-L-Ala-Gly-L-Cys-L-Lys-L-Asn-L-Phe-L-Phe-X-Trp-L-Lys-L-Thr-L-Phe-L-Thr-L-Ser-L-Cys-OH. If desired, the fully protected heptadecapeptide may be removed from the Resin support by aminolysis employing ammonia, dimethylamine, methylamine, ethylamine, n-propylamine, i-propylamine, butylamine, iso-butylamine, pentylamine, or phenethylamine, to yield the 17-Cysteine amide of the fully protected linear heptadecapeptide. The protecting groups may then be removed by treatment with liquid HF in the presence of anisole or by catalytic (e.g. Pd on BaSO$_4$) hydrogenation under conditions avoiding attack of the tryptophan moiety. Where the simple amide is the desired product, it may be produced directly by employing a benzhydrylamine resin via the technique disclosed by Rivaille et al. Helv. Chim. Acta, 54, 2772 (1971).

The deprotected linear heptadecapeptide and the corresponding amides are readily converted to the [6-17]cyclic disulfide (H-Phe-Phe-Phe-Ala)$^1$-Somatostatin derivative by mild oxidation (e.g. air), preferably through exposure of a solution of the linear compound to atmospheric oxygen. The protamine zinc and protamine aluminum complexes and non-toxic acid addition salts are produced by methods conventional in the polypeptide art.

Thus the intermediates which constitute part of this invention may be represented as:

R$^1$-Phe-Phe-Phe-Ala-Gly-Cys (R$^2$)-Lys (R$^3$)-Asn-Phe-Phe-X-Trp-Lys (R$^4$)-Thr (R$^5$)-Phe-Thr (R$^6$)-Ser (R$^7$)-Cys (R$^8$)-A, in which A represents —OH, —NH$_2$, dimethylamine, alkylamino of 1 to 5 carbon atoms or phenethylamine;

X represents the D- or L-configuration of the tryptophyl moiety;

R$^1$ represents hydrogen or an α-amino protecting group;

R$^2$ and R$^8$ are protecting groups for the sulfhydryl group of the two cysteinyl moieties, independently selected from the group consisting of 3,4-dimethylbenzyl and p-methoxy-benzyl;

R$^3$ and R$^4$ are protecting groups for the epsilon amino group of the two lysyl moieties selected from benzyloxycarbonyl, 2-chlorobenzyloxycarbonyl and 4-nitrobenzyloxycarbonyl;

$R^5$, $R^6$ and $R^7$ are benzyl.

The α-amino protecting group represented by $R^1$ may be any group known in the art to be useful in the stepwise synthesis of polypeptides. Illustrative of these known groups for protection of an α-amino group are (a) acyl type protective groups such as formyl, trifluoroacetyl, phthalyl, toluenesulfonyl (tosyl), benzenesulfonyl, nitrophenylsulfenyl, tritylsulfenyl, o-nitrophenoxyacetyl, chloroacetyl, acetyl, α-chlorobutyryl, and the like; (b) urethan type protecting groups such as benzyloxycarbonyl and substituted benzyloxycarbonyl (p-chlorobenzyloxycarbonyl, p-nitrobenzyloxycarbonyl, p-bromobenzyloxycarbonyl, p-methoxybenzyloxycarbonyl, tert-butyloxycarbonyl, diisopropylmethoxycarbonyl, isopropyloxycarbonyl, ethoxycarbonyl, allyloxycarbonyl, cyclopentyloxycarbonyl, adamantyloxycarbonyl, cyclohexyloxycarbonyl, phenylthiocarbonyl, and the like; (c) aralkyl type protecting groups as illustrated by triphenylmethyl, benzyl, and the like; and (d) trialkylsilane groups such as trimethylsilane. The preferred α-amino protecting groups defined by $R^1$ and employed with each amino acid introduced into the polypeptide is tertbutyloxycarbonyl.

The criterion for selecting protecting groups for $R^{2-8}$ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis of the desired amino acid sequence, under reaction conditions that will not alter the peptide chain.

The group —O—CH$_2$-[polystyrene resin support] defining A in the intermediates of this invention described supra, represents the ester moiety of one of the many functional groups of the polystyrene resin support.

The protamine zinc or protamine aluminum derivatives of the heptadecapeptide represent derivatives conventionally derived from polypeptides for characterization and administrative purposes. The acid addition salts of the heptadecapeptide are derived from both inorganic and organic acids known to afford pharmaceutically acceptable non-toxic addition products, such as hydrochloric, hydrobromic, sulfuric, phosphoric, maleic, acetic, citric, benzoic, succinic, malic, asorcbic and the like.

The in vivo activity of the compounds of this invention was established by subjecting (Phe$_3$-Ala)$^1$-Somatostatin, as a representative compound of this invention, to the following standard test procedure: three groups of ten albino male rats were arranged to provide a control group, a group for observation of Somatostatin activity as the standard and a group for the study of the test compound from Example 3-(Phe$_3$-Ala)$^1$-Somatostatin. Nembutal (50 mg/kg) was injected intraperitoneally into each rat. Fifteen minutes later a subcutaneous injection of the test compound, somatostatin (200 μg/kg) and physiological saline (control) was administered separately to each of the three groups of rats. Ten minutes later 0.5 milliliters of arginine (300 mg/ml, pH 7.2) was injected into the rats heart. The rats were decapitated five minutes later and their blood was collected in Trasylol -EDTA. Aliquot samples were radioimmunoassayed for growth hormone, glucagon and insulin. The cyclic heptadecapeptide of this invention, with Trp in the L-configuration and in the form of the C-terminal carboxylic acid, selected as representative of the group of compounds disclosed for test purposes, was employed in two additional distinct test procedures at about 5,000 μg/kg dose levels. The results of these tests are as follows:

| Compound | Dose μg/kg | GH ng/ml | Insulin μU/ml | Glucagon pg/ml | No Animals |
|---|---|---|---|---|---|
| Example 3 | 1,000 | 124±11 | 204±18* | 0.6±0.2 | 10 |
| SRIF | 200 | 117±6 | 136±12 | 2.0±1.4 | 10 |
| Control | — | 282±31 | 243±20 | 17.1±4.8 | 10 |
| Example 3 | 5,000 | 27±2 | 202±37* | 6.5±2.3 | 10 |
| Control | — | 126±25 | 283±37 | 14.0±3 | 20 |
| Example 3 | 4,660 | 97±7 | 165±16* | 1.1±0.5* | 10 |
| Control | — | 202±26 | 176±1 | 3.7±1.3 | 10 |

*Not Significant

Thus, the compounds of this invention are comparable in activity to somatostatin itself and are effective substitutes for somatostatin in the treatment of diabetes mellitus and acromegaly, even though the heptadecapeptides of this invention contain more amino acid residues than somatostatin.

Administration of the heptadecapeptides of this invention may be by conventional routes common to somatostatin and related polypeptides, under the guidance of a physician, orally or parenterally, in an amount dictated by the extent of the dysfunction as determined by the physician. The compound may be administered alone or in conjunction with conventional pharmaceutically acceptable carriers and adjuvants, in unit dosage form containing from about 2 to about 100 milligrams per kilogram host body weight. Furthermore, the protamine zinc or protamine aluminum adducts present desireable administrable forms of the heptadecapeptide as in conventional in therapy involving the use of polypeptides.

EXAMPLE 1 t-Butyloxycarbonyl-L-phenylalanyl-L-phenylalanyl-L-phenylalanyl-L-alanylglycyl-S-P-methoxybenzyl-L-cysteinyl-N$^\epsilon$ -(2-chlorobenzyloxycarbonyl)-L-lysyl-L-asparaginyl-L-phenylalanyl-L-phenylalanyl-L-tryptophyl-N$^\epsilon$ -(2-chlorobenzyloxycarbonyl)-L-lysyl-O-benzyl-L-threonyl-L-phenylalanyl-O-benzyl-L-threonyl-O-benzyl-L-seryl-3,4-dimethylbenzyl-L-cysteinyl methylated polystyrene resin.

To a 3 liter reaction vessel is added t-Boc(tertiary butyloxycarbonyl)-3,4 dimethylbenzyl-L-cysteine methylated polystyrene resin (240 g., 180 m moles) having a substitution of 0.75 m moles amino acid/g resin. The above substituted resin was prepared by the method of B. F. Gisin, Helvetica Chemica Acta 56, 1476, (1973). The resin was then treated in the following manner:

1. methanol (twice)
2. methylene chloride (twice)
3. 5 minute prewash with 1:1 trifluoroacetic acid-methylene chloride (v/v) containing 0.5% dithioerythritol
4. two consecutive 15 minute treatments with the above described trifluoroacetic acid
5. methylene chloride (twice)
6. dimethylformamide (twice)
7. two 10 minute treatments with 15% triethylamine in dimethylformamide 8. dimethylformamide (three times)
9. 20 minute methylene chloride wash
10. methanol (twice)
11. methylene chloride (twice)

A contact time of 5 minutes is allowed for each wash unless otherwise indicated.

The resin is gently stirred with t-Boc-O-benzyl-L-threonyl-O-benzyl-L-serine (175 g., 360 m moles in dimethylformamide containing 55.1 g., 360 m moles of 1-hydroxybenzotriazole) and 360 ml. of 1 M dicyclohexylcarbodiimide (DCC) in methylene chloride. After stirring overnight the peptide-resin is washed successively with dimethylformamide, methanol, methylene chloride (three times each). To test for completeness of reaction the peptide resin is subjected to a ninhydrin color test following the procedure of E. Kaiser, et al., Analytical Chemistry 34, 595 (1970) and found to be negative. A 2.5 g. portion of peptide-resin was removed and the synthesis continued.

Removal of the t-Boc α-amino protecting group is carried out as described in steps (3) through (11) above.

The following amino acid residues are then introduced consecutively:

t-Boc-L-Phenylalanine (63.6 g., 240 m moles in 1:1 methylene chloride-dimethylformamide, 240 m moles DCC). An 8.5 g. portion of peptide bound resin was removed at the completion of the cycle and the synthesis continued with the addition of t-Boc-O-benzyl-L-threonine (74.2 g., 240 m moles, in 1:1 methylene chloride-dimethylformamide, 240 m moles DCC), t-Boc-N$^\epsilon$ -(2-chlorobenzyloxycarbonyl)-L-lysine (99.5 g., 240 m moles in 1:1 methylene chloride-dimethylformamide, 240 m moles DCC). A 10 g. sample was removed and synthesis continued with the addition of t-Boc-L-tryptophane (73.0 g. 240 m moles, in dimethylformamide, 240 m moles DCC). A 20 g. sample was removed and the synthesis continued with the addition of t-Boc-L-phenylalanine (63.6 g., 240 m moles in 1:1 methylene chloride-dimethylformamide, 240 m moles DCC), t-Boc-L-phenylalanine (63.6 g., 240 m moles in 1:1 methylene chloride-dimethylformamide, 240 m moles DCC). A 14.7 g. sample was removed and the synthesis continued with the addition of t-Boc-L-asparagine-p-nitrophenylester (101.6 g., 290 m moles in 1% acetic acid-dimethylformamide, 48 hour coupling). The reaction time for each of the above couplings is 18 hours unless noted otherwise. Following each coupling the peptide resin is washed as described above. Removal of the α-amino protecting group (t-Boc) at each step is performed as described in steps 3-11, supra. The washed decapeptide-resin is dried (329.5 g.) and the synthesis continued with 66% (216 g.) of the peptide resin. After the addition of t-Boc-N$^\epsilon$ -(2-chlorobenzyloxycarbonyl)-L-lysine (66.3 g., 160 m moles in 1:1 methylene chloride-dimethylformamide, 160 m moles DCC) the resin is washed and the synthesis continued on an 5.0 sample of the undecapeptide-resin. The following amino acid residues are further introduced: t-Boc-S-p-methoxybenzyl-L-cysteine (2.0 g., 6 m moles in methylene chloride, 6.6 m moles DCC), t-Boc-alanylglycine (1.5 g., 6 m moles in dimethylformamide, 6.6 m moles DCC), t-Boc-phenylalanine (1.6 g., 6 m moles in methylene chloride, 6.6 m moles DCC), t-Boc-phenylalanine (1.6 g., 6 m moles in methylene chloride, 6.6 m moles DCC), t-Boc-phenylalanine (1.6 g., 6 m moles in methylene chloride, 6.6 m moles DCC). After washing the resin is dried in vacuo to yield 6.4 g.

Following the identical procedure, with substitution of t-Boc-D-tryptophane for t-Boc-L-tryptophane, there is produced the D-trp analogue of the title compound.

Alternatively, the peptide resin produce of Example 1 containing either L-trp or D-trp is removed from the resin support by treatment with an amine of the formula

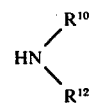

in which $R^{10}$ and $R^{12}$ are hydrogen or methyl or $R^{10}$ is hydrogen and $R^{12}$ is methyl, ethyl, propyl, isopropyl, butyl, secondary butyl, pentyl, or phenethyl followed by removal of any excess of the amine to yield the intermediate

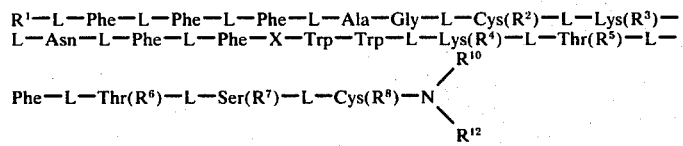

in which the groups $R^1$-$R^8$ are defined, supra, and $R^{10}$ and $R^{12}$ are hydrogen or methyl or $R^{10}$ is hydrogen and $R^{12}$ is alkyl of 1 to 5 carbon atoms or phenethyl.

The fully protected intermediate amide is then deprotected with liquid HF in the presence of anisole to yield

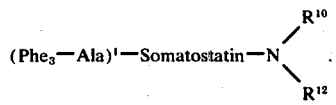

Thus, the protected peptide resin product of Example 1 (4.0 g.) in anhydrous ethylamine (143 ml.) is stirred at room temperature for 18 hours in a glass pressure bottle. The product is filtered, washed with dimethylformamide (three times) and the combined filtrate and washings is concentrated in vacuo to yield the fully protected derivative of (Phe$_3$-Ala)$^1$-somatostatin-NHC$_2$H$_5$, which is treated with liquid HF (40 ml.) and anisole (9.3 ml.) in vacuo at ice bath temperature for 1 hour. The HF is removed as quickly as possible. Degassed water (300 ml. × 2) is added to the residue and extracted with diethyl ether. The combined aqueous layer is lyophilized to yield fully deprotected Phe$_3$-Ala)$^1$-somatostatin-NHC$_2$H$_5$.

EXAMPLE 2

L-Phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine, (6 → 17), triacetate (Phe$_3$-Ala)$^1$-Somatostatin prepared in Example 1 (3.2 g.) is treated in vacuo with anhydrous liquid hydrogen fluoride (100 ml) and anisole (10 ml) at 0° for 45 minutes. The hydrogen fluoride and anisole are removed under reduced pressure and the residue suspended in anhydrous diethyl ether and filtered. The residue is then suspended in 2N acetic acid (75 ml), filtered and further washed with water (500 ml). The aqueous filtrates are combined, diluted with water (6.0l) and the pH adjusted to 6.8 with ammonium hydroxide. After 72 hours at +5° C. the solution is lyophilized twice to leave the above titled product (2.0 g).

The corresponding D-Trp analogue and the amides described in Example 1 readily cyclize under the same conditions.

EXAMPLE 3

Purification and characterization of L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine, (6 → 17) triacetate.

The above titled crude product is purified as follows: 2.0 g. of material is dissolved in a minimum amount of glacial acetic acid and applied to a column (2.5 × 200 cm) of Sephadex G-25 (fine) in glacial acetic acid. The column effluent is monitored by the Folin-Lowry color reaction on every third fraction (99 drops each). Fractions 177–222 are combined and lyophilized to yield 190 mg. of product. The material is shown to be homogenous by thin layer chromatography systems 4:1:5 (n-butanol: acetic acid: water) and 7:7:6 (isoamyl alcohol: pyridine: water). Thin layer chromatograms are visualized with iodine and chlorine peptide reagent.

R$_f$ 4:1:5 cellulose 0.63; silica gel 0.32
R$_f$ 7:7:6 cellulose 0.76; silica gel 0.67

Essentially the same purification technique is employed in the purification of the D-Trp analogue and the amides of the described heptadecapeptides.

What is claimed is:
1. A compound selected from the group consisting of

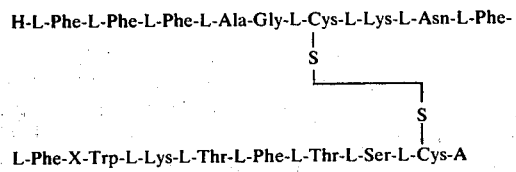

in which A is OH, —NH$_2$, dimethylamino, alkylamino of 1 to 5 carbon atoms or phenethylamino; X represents the D- or L-configuration of the tryptophyl moiety, the corresponding linear heptadecapeptide, the protamine zinc, protamine aluminum and non-toxic acid addition salts thereof.

2. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine.

3. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteine.

4. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine ethylamide.

5. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine ethylamide.

6. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine [6 → 17 disulfide].

7. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteine [6 → 17 disulfide].

8. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-L-tryptophyl-L-lysyl-L-threonyl-L-phenylalanyl-L-threonyl-L-seryl-L-cysteine [6 → 17 disulfide] ethylamide.

9. The heptadecapeptide of claim 1 which is L-phenylalanyl-L-phenylalanyl-L-phenylalanyl-L-alanylglycyl-L-cysteinyl-L-lysyl-L-asparaginyl-L-phenylalanyl-L-phenylalanyl-D-tryptophyl-L-lysyl-L-threonyl-L-phenylalanyl-L-threonyl-L-seryl-L-cysteine [6 → 17 disulfide] ethylamide.

10. A compound of the formula
R$^1$-L-Phe-L-Phe-L-Phe-L-Ala-Gly-L-Cys(R$^2$)-L-Lys(R$^3$)-L-Asn-L-Phe-L-Phe-X-Trp-L-Lys(R$^4$)-L-Thr(R$^5$)-L-Phe-L-Thr(R$^6$)-L-Ser(R$^7$)-L-Cys(R$^8$)-O-CH$_2$-[polystyrene resin support] in which X represents the D- or L-configuration of the tryptophyl moiety;

R$^1$ represents hydrogen or an α-amino protecting group;

R$^2$ and R$^8$ are protecting groups for the sulfhydryl group of the two cysteinyl moieties, independently selected from the group consisting of 3,4-dimethylbenzyl and p-methoxy-benzyl;

R$^3$ and R$^4$ are protecting groups for the epsilon amino group of the two lysyl moieties selected from benzyloxycarbonyl, 2-chlorobenzyloxycarbonyl and 4-nitrobenzyloxycarbonyl;

R$^5$, R$^6$ and R$^7$ are benzyl.

11. A compound of the formula
R$^1$-L-Phe-L-Phe-L-Phe-L-Ala-Gly-L-Cys-(R$^2$)-L-Lys(R$^3$)-L-Asn-L-Phe-L-Phe-X-Trp-L-Lys(R$^4$)-L-Thr(R$^5$)-L-Phe-L-Thr(R$^6$)-L-Ser(R$^7$)-L-Cys(R$^8$)-A in which
X represents the D- or L-configuration of the tryptophyl moiety;
A is OH, -NH$_2$, dimethylamino, alkylamino of 1–5 carbon atoms as phenethylamino;
R$^1$ represents hydrogen or an α-amino protecting group;
R$^2$ and R$^8$ are protecting groups for the sulfhydryl group of the two cysteinyl moieties, independently selected from the group consisting of 3,4-dimethyl-benzyl and p-methoxy-benzyl;
R$^3$ and R$^4$ are protecting groups for the epsilon amino group of the two lysyl moieties selected from benzyloxycarbonyl, 2-chlorobenzyloxycarbonyl and 4-nitrobenzyloxycarbonyl;
R$^5$, R$^6$ and R$^7$ are benzyl.

\* \* \* \* \*